United States Patent [19]
Morford et al.

[11] Patent Number: 6,068,894
[45] Date of Patent: May 30, 2000

[54] EUCALYPTUS FLORAL PRODUCT

[76] Inventors: Melaine Morford; Bruce Morford, both of 40 Island Rd., White Swan, Wash. 98952

[21] Appl. No.: 09/330,511

[22] Filed: Jun. 11, 1999

[51] Int. Cl.[7] .................................................. A01N 3/00
[52] U.S. Cl. ................................ 428/22; 428/15; 428/17; 428/23; 428/24; 156/61
[58] Field of Search ......................... 156/61, 63; 428/15, 428/17, 22, 23, 24

[56] References Cited

U.S. PATENT DOCUMENTS

| | | | |
|---|---|---|---|
| 1,588,274 | 6/1926 | Schlosser . | |
| 4,293,601 | 10/1981 | Cole | 428/24 |
| 4,600,612 | 7/1986 | Litwin et al. | 428/23 |
| 4,788,085 | 11/1988 | DeLuca et al. | 428/18 |
| 5,310,585 | 5/1994 | Haagenson . | |

*Primary Examiner*—Francis J. Lorin
*Assistant Examiner*—Wendy Boss
*Attorney, Agent, or Firm*—Stratton Ballew PLLC

[57] ABSTRACT

A eucalyptus floral product and a method for producing the same is provided. The floral product is non-perishable and permanent, while appearing to be naturally grown as opposed to artificially manufactured. The eucalyptus leaf floral product comprises a plurality of eucalyptus leaves attached to a central stem to substantially resemble a corolla. Additionally, the corolla preferably resembles a rosette. The central stem is preferably a length of wire, and the eucalyptus leaves are preferably preserved eucalyptus leaves. The corolla includes an underside, and a plurality of smaller eucalyptus leaves attached to the underside of the corolla form to substantially resemble a calyx. Additionally, the leaves can be soaked in a mildly acidic solution, such as vinegar, before the leaves are formed into the floral product.

27 Claims, 6 Drawing Sheets

EUCALYPTUS FLORAL PRODUCT

TECHNICAL FIELD

The invention relates to a decorative floral product, and more particularly to a method for forming eucalyptus leaves to resemble a flower.

BACKGROUND OF THE INVENTION

The floral product industry is well established and utilizes a wide variety of materials to manufacture aesthetically pleasing arrangements. These arrangements can include wreaths, swags, bouquets, centerpieces and ornaments. The utilization of preserved and long-lasting materials is desirable because floral arrangements require significant labor to manufacture and their value increases if the arrangement is long lasting and permanent, as opposed to perishable and disposable.

A popular material for floral arrangements is eucalyptus. The eucalyptus has aromatic leaves that are pleasantly configured and easily preserved. Even when the eucalyptus leaf is preserved it continues to dispense its pleasing aroma. There are well more than 1,500 varieties of eucalyptus. Branches or sprigs of certain varieties eucalyptus are commonly preserved systemically with glycol or glycerine. Systemically preserved eucalyptus sprigs are widely incorporated into many floral decorations and arrangements.

Most preserved floral products, such as preserved sprigs of eucalyptus, cannot be employed as central or focus elements of a particular arrangement. This is because it is desirable to have a focus element that is larger and more complex than the surrounding elements of the arrangement Flowers, or flower-like products often occupy the focal points of an arrangement. Artificial flowers, which are desirable for non-perishable arrangements, are typically very expensive, because true, life-like flowers are very difficult to fabricate.

Therefore, a focal point flower-like or floral product is needed that is non-perishable, and relatively easy to fabricate. Relatedly, a focal point floral product is needed that appears to be naturally grown as opposed to artificially manufactured.

SUMMARY OF INVENTION

The invention provides a eucalyptus floral product and a method for producing the same. According to one aspect of the invention, a floral product is provided that is non-perishable and permanent. According to a related aspect of the invention, a floral product is provided that appears to be naturally grown as opposed to artificially manufactured.

Specifically, the invention provides a eucalyptus leaf floral product that comprises a plurality of eucalyptus leaves attached to a central stem to substantially resemble a corolla in form. Additionally, the corolla preferably resembles a rosette.

In a preferred embodiment of the present invention, the central stem is preferably a length of wire, and the eucalyptus leaves are preferably preserved eucalyptus leaves.

In an additional preferred embodiment of the present invention, the corolla form includes an underside, and a plurality of smaller eucalyptus leaves attached to the underside of the corolla form to substantially resemble a calyx in form.

The method of the present invention produces a eucalyptus leaf floral product. The method includes removing a plurality of leaves from a eucalyptus sprig. The removed leaves are then individually attached around a main support to form a corolla in a pattern that is substantially similar to a rosette.

Next, the preferred method of the invention can include the attachment of the smaller eucalyptus leaves to the underside of the corolla to substantially resemble a calyx in form.

As a preferred additional step of the present invention, the plurality of leaves used to form the floral product are sorted for size, shape and condition after the leaves are removed from the eucalyptus sprig. Additionally, the leaves can be soaked in an acidic solution before the leaves are formed into the floral product.

DETAILED DESCRIPTION OF SPECIFIC EMBODIMENTS

The invention provides a decorative floral product made with eucalyptus foliage. The invention additionally includes a method for producing or manufacturing the decorative floral product. The decorative floral product is essentially a manufactured article having the appearance of a rosette. A rosette is defined herein as a radiating cluster of leaves or petals, which substantially resembles or suggests a bloom of a petaled flower, such as rose or camellia.

Figure 1:
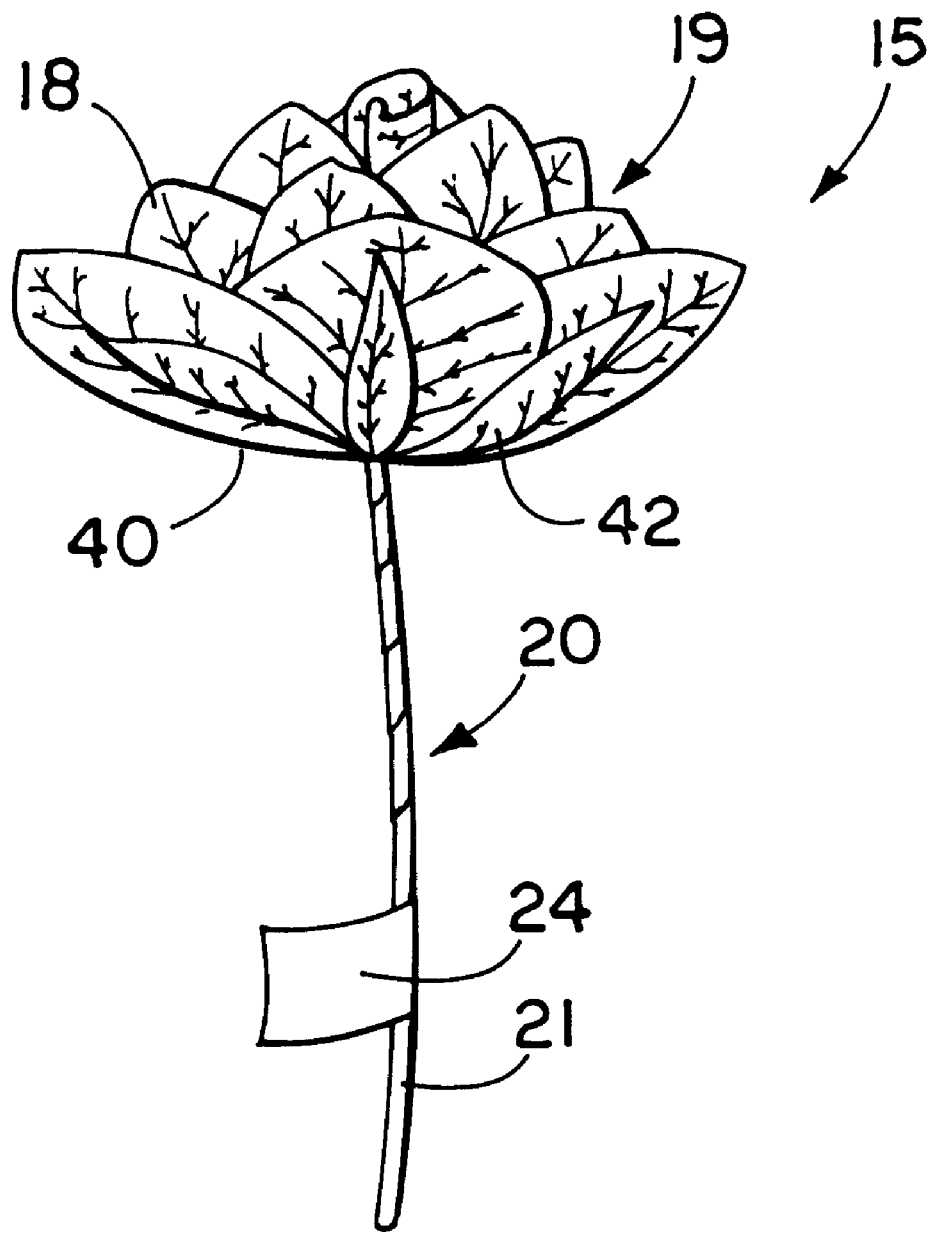
FIG. 1 is a side view of a eucalyptus leaf floral product, according to an embodiment of this invention.

A preferred embodiment of the present invention is illustrated in the attached FIGS. 1 through 11. A eucalyptus leaf floral product 15 is shown in FIG. 1, which includes a plurality of eucalyptus leaves 18, each attached proximate a central stem 20. The eucalyptus leaves are arranged in a radiating pattern, to substantially resemble the collective petals of a flower, which in botanical terms can be referred to, and are referred to herein, as a corolla 19.

Figure 11:
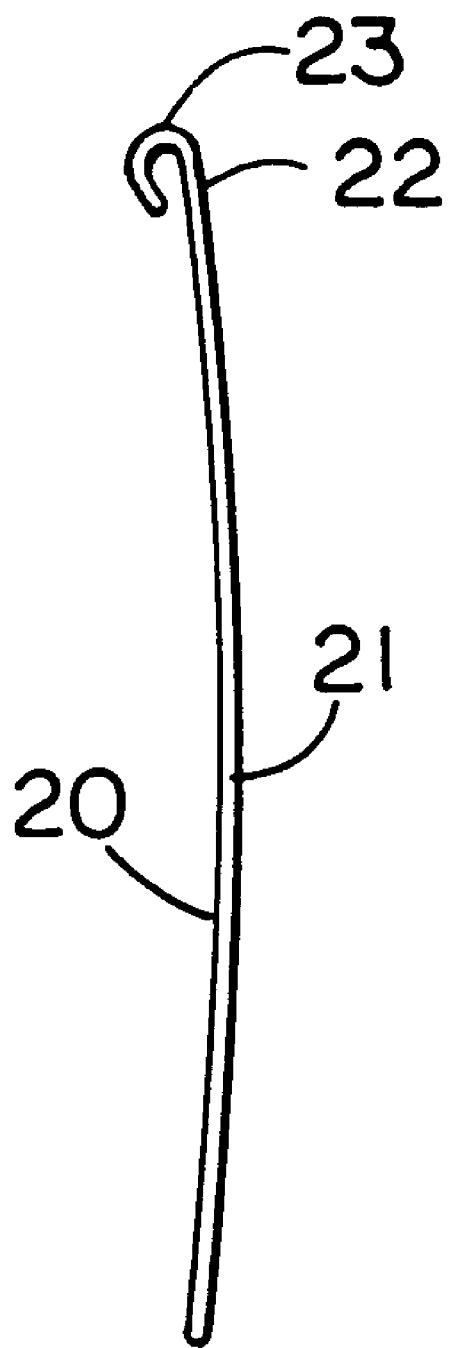
FIG. 11 is a side view of a portion of eucalyptus leaf floral product, according to an embodiment of this invention.

The central stem 20 is utilized as a central frame element. The central stem is preferably a floral wire 21 having a suitably heavy gauge. A standard #18 gauge of floral wire is preferred in order to maintain a rigid vertical position, and simultaneously allow for curving and positioning the flower in design applications or arrangements. As shown in FIGS. 6B and 11, the floral wire has a floral end 22 for receiving the corolla. A small loop 23 is preferably formed at an end of the floral wire. The small loop aids in the attachment of the corolla 19 to the central stem. Additionally, as shown in FIG. 1, the central stem is preferably wrapped in a tape material 24, which is most preferably a length of conventional cloth floral tape.

Figure 2:
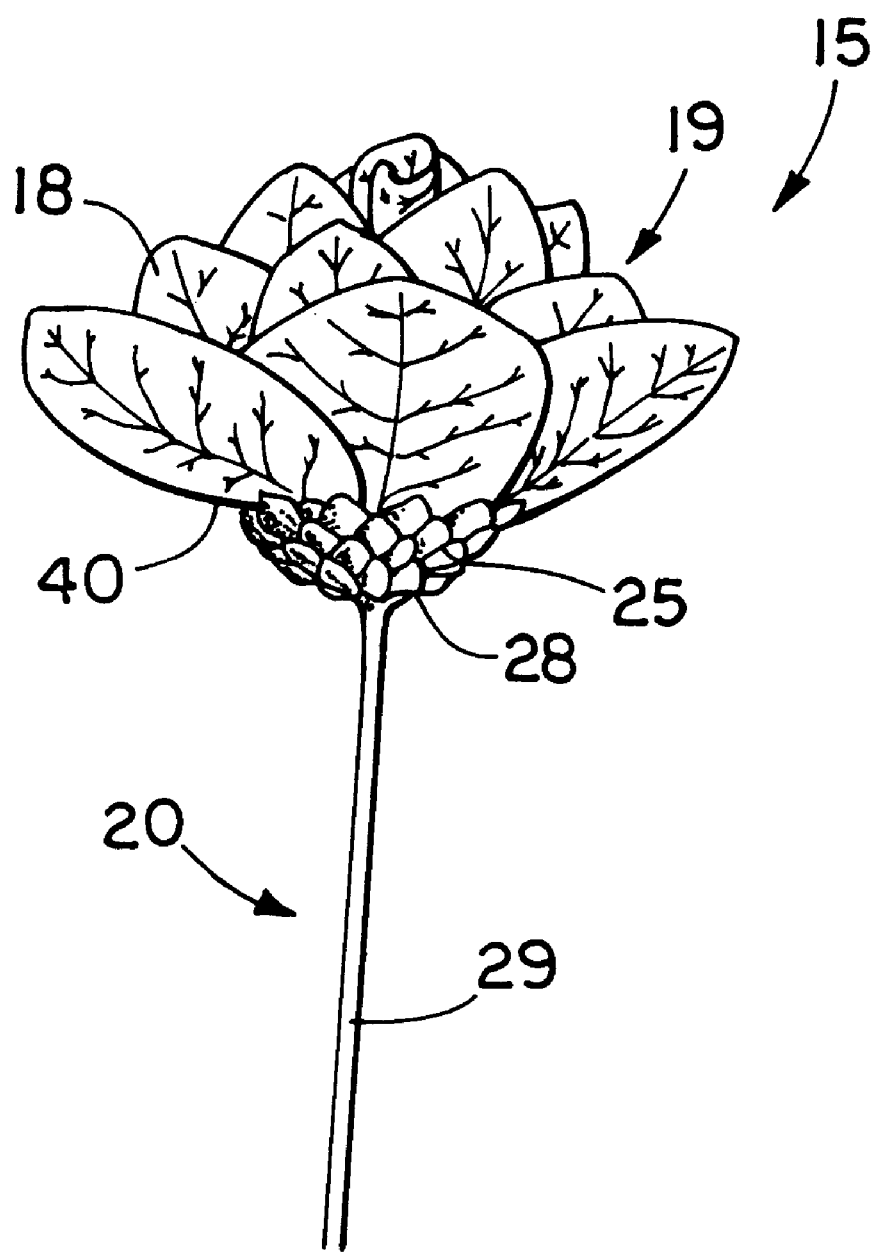
FIG. 2 is a side view of a eucalyptus leaf floral product, according to an embodiment of this invention.

Alternatively, the central stem 20 can be a dried flower stem, a twig or a decorative pipe cleaner. In a preferable alternative, as shown in FIG. 2, the central stem can be an involucre 25. The involucre is defined herein as a whorl of bracts subtending a flower or flower cluster. Most preferably, the involucre is a preserved involucre, and includes a base 28 with a stem member 29 extending from the base of involucre.

Although there may be more than 1,500 varieties of eucalyptus, a most desirable variety for creating the floral product 15 of the present invention is the spiral eucalyptus, known as *Eucalyptus cinerea,* or *Eucalyptus pulverulenta,* and is preferred because their leaves resemble the petals of a full, open rose.

The leaves of the spiral eucalyptus resemble the petals of a flower, especially the petals of a rose. The leaves of the preserved eucalyptus sprigs, once removed, can be assembled into the pleasing floral product of the present invention. Although untreated and unpreserved eucalyptus leaves could be employed, eucalyptus branches or sprigs preserved systematically with glycol perform as excellent raw materials for constructing the floral product of the present invention. Additionally, the eucalyptus can be systemically dyed to change or enhance the color of the eucalyptus leaves. Preferably a red dye can be introduced into the preserving solution to make the leaves more closely resemble the petals of a red rose. Alternatively, other pigments can be employed, such as green, blue or yellow. Also alternatively, paints, powders or externally applied dyes or rinses can be applied to the leaves to give them a wide variety of alternative appearances, as desired.

The leaves 18 of the eucalyptus are removed by holding the stem of the eucalyptus in one hand and, starting at the bottom of the stem, moving the thumb and index finger of the opposite hand down the stem. A rose thorn "stripper" tool, also works well in removing the eucalyptus leaves.

Figure 6A:
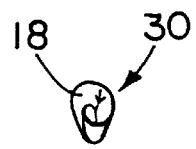
FIG. 6A is a top view of a portion of a eucalyptus leaf floral product, according to an embodiment of this invention.
Figure 6B:
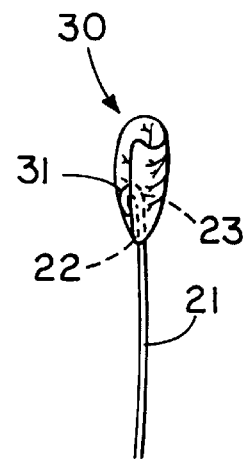
FIG. 6B is a side view of a portion of a eucalyptus leaf floral product, according to an embodiment of this invention.

To form the floral product 15 of the present invention, a smaller leaf 18 is selected to comprise a floral center 30, as shown in FIGS. 6A and 6B. The floral center is attached to the small loop 23 at the floral end 22 of the floral wire 21. A glue 31 is utilized to adhere the floral center to the small loop. Preferably, a hot-melt, quick-drying type of glue is suggested, and stick formed glue as dispensed by a typical hot glue gun is most preferred.

Figure 7A:
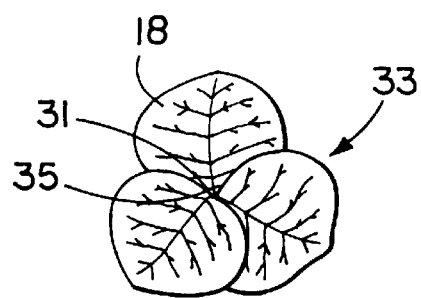
FIG. 7A is a top view of a portion of a eucalyptus leaf floral product, according to an embodiment of this invention.
Figure 7B:
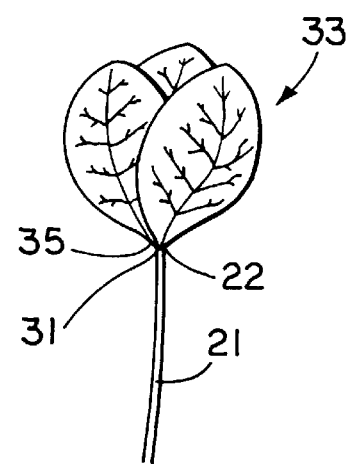
FIG. 7B is a side view of a portion of a eucalyptus leaf floral product, according to an embodiment of this invention.

FIGS. 7A and 7B shows a first tier 33 of the eucalyptus leaves 18 arranged to attach to the central stem 20. Each of the leaves includes a base 35. The base is herein defined as the portion of the eucalyptus leaf proximate to the leaf's attachment to its sprig or branch. For eucalyptus leaves, this base is often amplexicaul in that the base of the leaf clasps or wraps around the stem. For the present invention, the leaves are detached from the sprig at their bases and then preferably attached with a small amount of the glue 31 applied at the base, proximate the central stem 20. FIG. 7B details the attachment of the first tier to the floral wire.

Figure 8A:
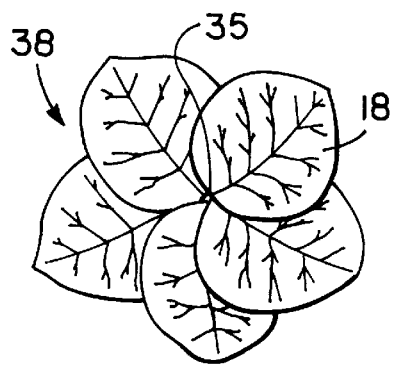
FIG. 8A is a top view of a portion of a eucalyptus leaf floral product, according to an embodiment of this invention.
Figure 8B:
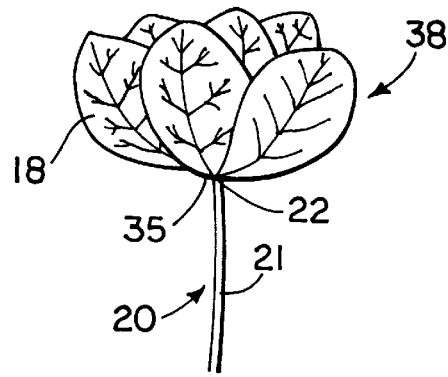
FIG. 8B is a side view of a portion of a eucalyptus leaf floral product, according to an embodiment of this invention.

FIG. 8A shows a second tier 38 of eucalyptus leaves 18. The second tier is arranged radially, like the first tier 33, to attach to the central stem 20. As detailed in FIG. 8B, the second tier is preferably attached with the glue 31 to the floral end 22 of the floral wire 21 and beneath the first tier.

Figure 9A:
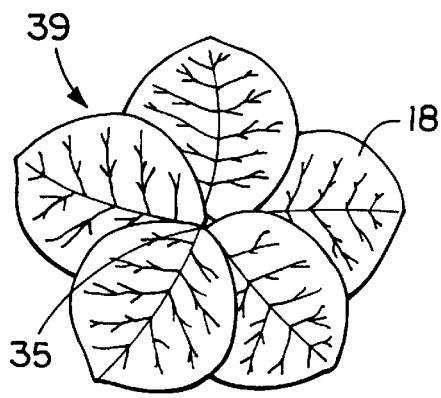
FIG. 9A is a top view of a portion of a eucalyptus leaf floral product, according to an embodiment of this invention.
Figure 9B:
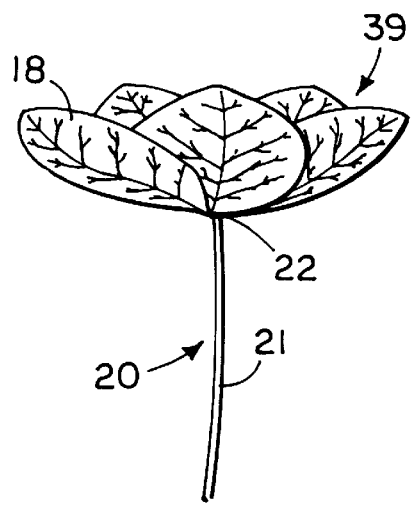
FIG. 9B is a side view of a portion of a eucalyptus leaf floral product, according to an embodiment of this invention.

FIG. 9A shows a third tier 39 of eucalyptus leaves 18. The third tier, like the first tier 33 and the second tier 38, also attaches to the central stem 20. FIG. 9B details the attachment of the third tier to the central stem, again preferably with a small amount of glue 31. The third tier is most preferably attached to the floral end 22 of the floral wire 21 beneath the second tier 38.

Figure 3:
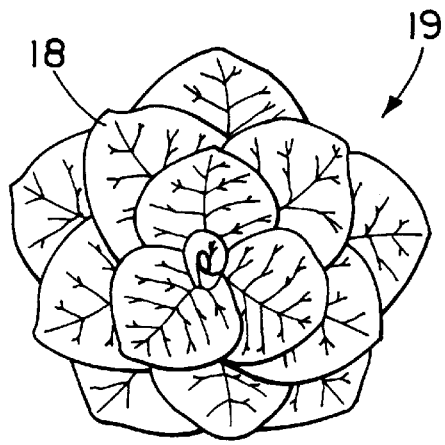
FIG. 3 is a is a top view of a eucalyptus leaf floral product, according to an embodiment of this invention.
Figure 4:
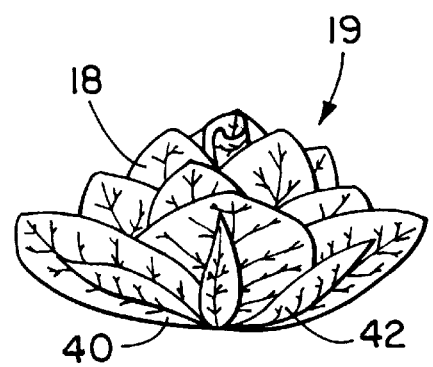
FIG. 4 is a side view of a portion of a eucalyptus leaf floral product, according to an embodiment of this invention.
Figure 5:
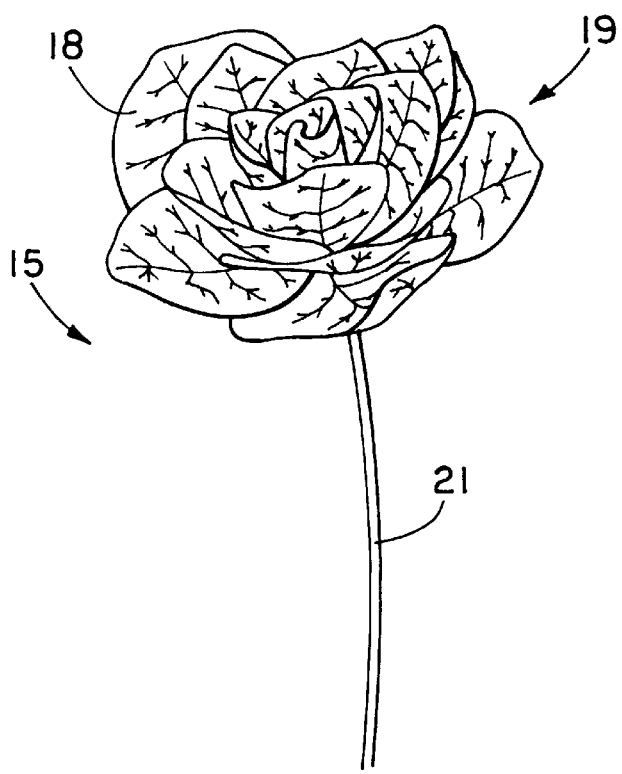
FIG. 5 is a perspective view of a eucalyptus leaf floral product, according to an embodiment of this invention.

FIG. 3 shows the corolla 19 of eucalyptus leaves 18 from the top and combines FIGS. 6A, 7A, 8A and 9A to show the floral product 15 in its finished form. The corolla includes an underside 40 as detailed in FIGS. 1, 2 and 4. A plurality of smaller eucalyptus leaves 18 attach to the underside of the corolla to form a calyx 42. FIG. 4 illustrates the corolla from the side and shows the preferred addition of the calyx to the floral product. The calyx is herein defined as a plurality of sepals, which are attached to the floral product of the present invention to resemble individual leaf-like sepal coverings of the flower bud.

Figure 10A:
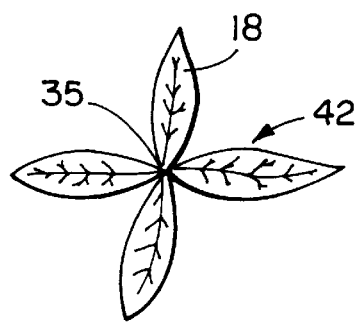
FIG. 10A is a top view of a portion of a eucalyptus leaf floral product, according to an embodiment of this invention.
Figure 10B:
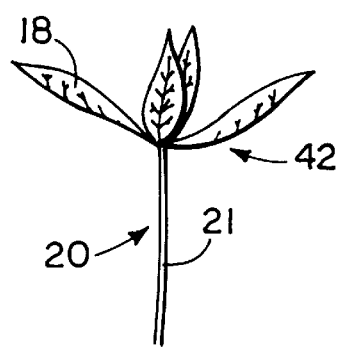
FIG. 10B is a side view of a portion of a eucalyptus leaf floral product, according to an embodiment of this invention.

The eucalyptus leaf 18 preferably utilized for the calyx is thin and long as compared with the leaves used for the first tier 33, the second tier 38, the third tier 39 and the floral center 20. The eucalyptus variety Mini-Teardrop is preferable for use in forming the calyx 42. FIG. 10A shows a top view of the calyx, as the bases 35 of the eucalyptus leaves are joined at the central stem 20. Again, the hot glue 31 is preferably employed for this task. A small amount of the glue is placed at the base of each leaf and an additional small amount can be placed along the leaf to help the it remain attached to the underside 40 of the corolla 19.

As an alternative to the calyx 42, the involucre 25 can be attached to the corolla 19. To achieve this attachment, the central stem 20 is preferably shortened to insert into the involucre and then glue 31, again most preferably from the hot glue gun, is utilized to attach and seat the corolla into the involucre, as shown in FIG. 2.

In a preferred method of the present invention, the eucalyptus leaves 18 are sorted after they are stripped from their branches. The size, shape and condition of the leaves determines the allocation for manufacturing. The smallest leaves will become the center petals of the flower, and the largest the outer petals. Also, if desired, the leaves can be sorted for the manufacturing of small, medium, or large floral products. The quality of the preserved eucalyptus leaves may be less than desirable for constructing the floral product. If a particular leaf is torn at an outer area that would be noticed, it is best to discard it during the sorting stage. This preliminary quality control step will alleviate the possibility of using inferior leafs in construction of the floral product 15 of the present invention.

As discussed above, the leaves that represent petals in the floral product 15 of the present invention consist of leaves 18 that are removed most preferably from preserved spiral eucalyptus foliage. The most appealing floral product is constructed to resemble a mature, open rose bloom. However, varying types or forms of flowers may be constructed with the preserved leaves of the eucalyptus, which includes the preferred spiral varieties. The size of the floral product is primarily determined by the size and shape of the leaves of the eucalyptus. For instance, the smaller the leaves, the smaller the diameter of the floral product.

The floral product 15 of the present invention may be constructed without any special preparation of the preserved eucalyptus leaves 18. It is preferred, however, that the preserved eucalyptus leaves, once removed from their original stem, are immersed in a solution to remove some of the oils from the surface of the leaves. Preferably, a mildly acidic solution, such as a vinegar and water solution is utilized; however, the solution may be any solution that is slightly acidic to effectively remove the surface oils from the individual eucalyptus leaves. Citric acid is specifically considered as an alternative to vinegar. Most preferably, the weak acid solution is a 1:1 mixture of water and vinegar. It is desirable to place each category of sized leaves in a separate bowl or container of the solution, so that the pre-sorting process in maintained. The leaves are submerged for approximately 10 to 15 minutes. After submersing the leaves in the solution the leaves are dried. Preferably the leaves are placed in a fabric bag, such as a conventional laundry bag, and the entire bag inserted into a laundry dryer for approximately 10 to 15 minutes, or until the leaves are dry to the touch. The eucalyptus leaves, once treated with the slightly acid solution, perform much better and maintain a satisfactory hold with the glue 31 or adhesive. The solution naturally only slightly permeates the surface of the leaves, thereby preventing saturation of the leaves. It is therefore possible to dry large quantities of the eucalyptus leaves at one time.

Once dried, the sorted, graded and sized leaves 18 are placed in separate containers. Their strategic placement is important for a cost-effective assembly of the flowers 15. The smallest petals are preferably placed at the beginning of a production line, then the medium sized and largest at the opposite end. It is alternatively possible to place the containers in a semi-circular position, around the individual who is constructing the flowers.

The floral wire 21 is formed into the central stem 20 for the floral product 15, as shown in FIG. 11. The floral end 22 of the wire is folded in a closed U-shape, or a loop 23, that is approximately ⅜" long. The U-shaped end acts as the center and mounting area for the center 30 of the flower, as shown in FIG. 6B. The length of the wire stem is optional. If the flower is being constructed for use as a focal compliment that will be set into a wreath or swag or other design not requiring a long stem, it is suggested that a length of 4 inches would be adequate for the latter application. If the flower is being used with complimenting foliage in a package or as part of a larger floral design or arrangement, a stem ranging from 18 to 24 inches is alternatively suggested.

To begin the actual construction or manufacture of the floral product 15, a relatively small leaf 18 is selected as the floral center. The U-shaped end 23 of the wire is placed in the center of the leaf, and a spot of hot glue 31, again preferably from a hot glue gun, is applied to the leaf and the floral wire 21. The outer, rounded edge of the leaf is folded over the U-shaped end of the wire, creating a visually pleasing center for the floral product. The floral center 30 is held together for a few seconds, until the glue is sufficiently dry.

Next, approximately three similar leaves 18 of a relatively small size are selected to form the first tier 33, as shown in FIG. 7B. Each is attached by gluing the bottom edge to the floral wire 21. As each leaf is added, it will usually overlap the previous leaf, near the base of the floral product 15, which is at the floral end 22 of the floral wire.

Next, approximately five small to medium leaves 18 are selected for a second tier 38 or row. These are then added to the partially constructed floral product 15. It is important to note that centering the leaves of each tier over the neighboring, adjacent rows is to be avoided. The flower would not have the appearance of a natural flower in nature if the tiers align or are centered one atop the other in an unnatural symmetry.

The next row or third tier 39 of leaves 18 consists of the medium to large leaves. Approximately five leaves are attached with hot glue in the same manner to the central stem 20. Again, as shown in the drawings, the separation and placement of the leaves is important to achieve a natural and pleasing form in the floral product 15.

Additional tiers of eucalyptus leaves 18 can be added to represent additional rows of flower petals, preferably comprising of larger sized leaves. The size of the floral product will continue to be enhanced with the continued addition of leaves. Excluding the floral center 30 and the calyx 4:2, the average number of leaves used to create an attractive corolla 19 is approximately 13 to 15 leaves.

Once the basic shape and style of the floral product 15 is completed, three small Mini Teardrop eucalyptus leaves 18 are attached to the underside 40 of the corolla 19, again with hot melt glue 31. The widest part of the leaf is attached to the central stem 30, and the tip of the leaf, which represents a sepal, radiates outward. It is suggested that five leaves are used when constructing a larger floral product. This step adds a realistic character to the floral product, and assists in covering the mechanics of construction.

If a more visually appealing or "finished" stem 21 is desired, the stem may be wrapped with floral tape 24, as shown in FIG. 1. The tape is attached by pinching the end of the floral tape around the underside 40 of the corolla 19 and twirling the wire, while maintaining the tape in a diagonal position on the wire, tightening the tape as the tape is moved downward on the wire. When the stem is wrapped as desired, the end of the tape is then tom and swirled to tighten.

The finished eucalyptus floral product 15 is now complete, with no further surface treatment. However, it may be noted that the application of metallic powdered paints, in conjunction with a mixture of water soluble varnish, will create a very attractive effect. Also, the use of other paint and stain applications will enhance and broaden the range of color, texture and variations. These alternative additions can significantly increase the potential demand and desirability of these flower forms all constructed of systemically preserved eucalyptus as described herein above.

In compliance with the statutes, the invention has been described in language more or less specific as to structural features and process steps. While this invention is susceptible to embodiment in different forms, the specification illustrates preferred embodiments of the invention with the understanding that the present disclosure is to be considered an exemplification of the principles of the invention, and the disclosure is not intended to limit the invention to the particular embodiments described. Those with ordinary skill in the art will appreciate that other embodiments and variations of the invention are possible which employ the same inventive concepts as described above. Therefore, the invention is not to be limited except by the following claims, as appropriately interpreted in accordance with the doctrine of equivalents.

What is claimed is:

1. A eucalyptus leaf floral product comprising:
   a plurality of eucalyptus leaves attached to a central stem to substantially resemble a corolla.

2. The eucalyptus leaf floral product of claim 1, wherein the eucalyptus leaves are preserved eucalyptus leaves.

3. The eucalyptus leaf floral product of claim 1, wherein the corolla resembles a rosette.

4. The eucalyptus leaf floral product of claim 1, wherein the central stem is wrapped with a tape material.

5. The eucalyptus leaf floral product of claim 1, wherein the central stem includes a preserved involucre.

6. The eucalyptus leaf floral product of claim 1, wherein the central stem is a length of wire.

7. The eucalyptus leaf floral product of claim 6, wherein the length of wire includes floral end and the floral end includes a small loop for receiving a floral center.

8. The eucalyptus leaf floral product of claim 7, wherein the floral center is a eucalyptus leaf.

9. The eucalyptus leaf floral product of claim 1, wherein the corolla form includes an underside, and a plurality of smaller eucalyptus leaves attached to the underside of the corolla form to substantially resemble a calyx.

10. A method for producing a eucalyptus leaf floral product comprising the steps of:
   a. removing a plurality of leaves from a eucalyptus sprig;
   b. individually attaching the leaves around a main support; and
   c. forming a corolla with the leaves.

11. The method for producing a eucalyptus leaf floral product of claim 10, wherein the step of forming a corolla with the leaves additionally includes:
   d. forming a pattern with the leaves around the main support that is substantially similar to a rosette.

12. The method for producing a eucalyptus leaf floral product of claim 10, additionally including the step of:
   d. attaching a plurality of smaller eucalyptus leaves to the underside of the corolla to substantially resemble a calyx.

13. The method for producing a eucalyptus leaf floral product of claim 10, wherein the step of individually attaching the leaves around a main support additionally includes:
   d. overlapping a previously attached leaf with a subsequently attached leaf.

14. The method for producing a eucalyptus leaf floral product of claim 10, including the step of:
   d. forming a main support from a wire length.

15. The method for producing a eucalyptus leaf floral product of claim 12 wherein the step of forming a main support from a wire length additionally includes:
   e. forming a small loop in the end of a wire.

16. The method for producing a eucalyptus leaf floral product of claim 12 wherein the step of forming a main support additionally includes:
   e. wrapping the main support with a tape material.

17. The method for producing a eucalyptus leaf floral product of claim 10, wherein the step of removing a plurality of leaves from a eucalyptus sprig additionally includes:
   sorting the leaves for size, shape and condition.

18. The method for producing a eucalyptus leaf floral product of claim 10, wherein the step of removing a plurality of leaves from a eucalyptus sprig additionally includes:
   d. soaking the leaves in an acidic solution; and
   e. drying the leaves.

19. A eucalyptus leaf floral product produced by the process steps of:
   a. removing a plurality of leaves from a eucalyptus sprig;
   b. individually attaching the leaves around a main support; and
   c. forming a corolla with the leaves.

20. The eucalyptus leaf floral product of claim 18, wherein the process step of forming a pattern with the leaves additionally includes:
   d. forming a pattern with the leaves around the main support that is substantially similar to a rosette.

21. The eucalyptus leaf floral product of claim 18, additionally including the process step of:
   d. attaching a plurality of smaller eucalyptus leaves to the underside of the corolla to substantially resemble a calyx.

22. The eucalyptus leaf floral product of claim 18, wherein the process step of individually attaching the leaves around a main support additionally includes:
   d. overlapping a previously attached leaf with a subsequently attached leaf.

23. The eucalyptus leaf floral product of claim 18, including the step of:
   d. forming the main support from a length of wire.

24. The method for producing a eucalyptus leaf floral product of claim 22 wherein the step of forming a main support additionally includes:
   e. forming a small loop in the end of a wire.

25. The method for producing a eucalyptus leaf floral product of claim 22 wherein the step of forming a main support additionally includes:
   e. wrapping the main support with a tape.

26. The method for producing a eucalyptus leaf floral product of claim 18, wherein the step of removing a plurality of leaves from a eucalyptus sprig additionally includes:
   d. sorting the leaves for size, shape and condition.

27. The method for producing a eucalyptus leaf floral product of claim 18, wherein the step of removing a plurality of leaves from a eucalyptus sprig additionally includes:
   d. soaking the leaves in an acidic solution; and
   e. drying the leaves.

* * * * *